United States Patent [19]

Haddad et al.

[11] Patent Number: 4,996,179

[45] Date of Patent: * Feb. 26, 1991

[54] MALEIC ANHYDRIDE CATALYSTS AND PROCESS FOR THEIR MANUFACTURE

[75] Inventors: Muin S. Haddad, Naperville; Bernard L. Meyers, Wheaton; William S. Eryman, Naperville, all of Ill.

[73] Assignee: Amoco Corporation, Chicago, Ill.

[ * ] Notice: The portion of the term of this patent subsequent to Jun. 12, 2007 has been disclaimed.

[21] Appl. No.: 484,342

[22] Filed: Feb. 22, 1990

Related U.S. Application Data

[63] Continuation-in-part of Ser. No. 297,329, Jan. 17, 1989, Pat. No. 4,933,312.

[51] Int. Cl.$^5$ .................................... B01J 27/198
[52] U.S. Cl. ........................................... 502/209
[58] Field of Search ................................ 502/209

[56] References Cited

U.S. PATENT DOCUMENTS

| | | | |
|---|---|---|---|
| 3,977,998 | 8/1976 | Freerks et al. | 502/209 |
| 4,396,535 | 8/1983 | Bremer et al. | 502/209 X |
| 4,699,895 | 10/1987 | Edwards | 502/209 |

*Primary Examiner*—W. J. Shine
*Attorney, Agent, or Firm*—Gunar J. Blumberg; William H. Magidson; Ralph C. Medhurst

[57] ABSTRACT

A catalyst comprising a phosphorus-vanadium mixed oxide and existing in the form of geometric shapes, such as tablets, provides minimum expansion of the geometric shapes under process reaction conditions, since the catalyst in the form of said geometric shapes has been heated in an inert atmosphere at a temperature within the range of about 343° C. (650° F.) to about 704° C. (1,300° F.) prior to being exposed to an oxygen-containing atmosphere at an elevated temperature. This catalyst is suitable for the oxidation of a hydrocarbon, such as benzene or n-butane, to maleic anhydride.

41 Claims, No Drawings

MALEIC ANHYDRIDE CATALYSTS AND PROCESS FOR THEIR MANUFACTURE

CROSS-REFERENCE TO RELATED APPLICATION

This application is a continuation-in-part application of U.S. Ser. No. 297,329, filed on Jan. 17, 1989, now U.S. Pat. No. 4,933,312, in the U.S. Patent and Trademark Office.

BACKGROUND OF THE INVENTION

1. Field of the Invention

This invention relates to novel catalysts comprising phosphorus-vanadium mixed oxides or phosphorus-vanadium-co-metal mixed oxides and to processes for the manufacture and use of such catalysts. More particularly, this invention relates to such catalysts which are suitable for the oxidation of hydrocarbon feedstocks comprising benzene, butane, butenes, butadiene, or mixtures thereof to maleic anhydride and to their method of manufacture.

2. Prior Art

Maleic anhydride is of significant commercial interest throughout the world and is extensively used in the manufacture of alkyd resins. It is also versatile intermediate for chemical synthesis. Consequently, large quantities of maleic anhydride are produced each year to satisfy these needs.

In general, catalysts proposed for the oxidation of butane to maleic anhydride have been based upon vanadium and phosphorus. In U.S. Pat. No. 3,293,268, it is disclosed that the oxidation of butane to maleic anhydride can be performed in the presence of a phosphorus-vanadium-oxygen-containing complex catalyst. Though this catalyst is capable of oxidizing butane, it does not give sufficiently high yields. Yields of maleic anhydride of only 30 to 50 weight percent are reported. Various activators, stabilizers, and promoters have been disclosed in the prior art to improve the yields of maleic anhydride. References include U.S. Pat. Nos. 3,867,411; 3,832,359; 3,888,886; 4,002,650; 4,147,661; 4,149,992; 4,151,116; 4,152,338; 4,152,339; 4,403,943; 4,154,703; and British Application No. 2,019,839A. While the aforementioned prior art tends to bring about some improvement in the performance of the phosphorus-vanadium catalyst, there remains much room for improvement, particularly from the standpoint of high conversion, yield, and catalyst life. Other references of interest include U.S. Pat. Nos. 4,020,174; 4,094,816; 4,089,807; 3,296,282; 3,474,041, and British Patent No. 1,464,198. All of these references relate to catalyst regeneration and not to catalyst stability.

Also, U.S. Pat. Nos. 3,915,892 and 3,985,775 teach a process for preparing catalysts suitable for preparing maleic anhydride from n-butane comprising a mixed vanadium-phosphorus oxide wherein one of the process steps consists of heating the components to between 350° C. (662° F.) and 410° C. (770° F.) in an oxygen-containing gas. The function of this step is to remove water of hydration from the dihydrate of the mixed oxide of the vanadium and pentavalent phosphorus complex.

SUMMARY OF THE INVENTION

According to the present invention, there is provided a catalyst for the production of maleic anhydride by the oxidation of a feedstock comprising a member selected from the group consisting of benzene, n-butane, butenes, butadiene, and mixtures thereof, which catalyst comprises a phosphorus-vanadium mixed oxide or a phosphorus-vanadium-co-metal mixed oxide and exists in the form of geometric shapes, said catalyst in the form of said shapes having been heated in an inert atmosphere at a temperature in the range of about 343° C. (650° F.) to about 704° C. (1,300° F.) prior to being exposed to an oxygen-containing atmosphere at an elevated temperature.

In addition, there is provided a process for the manufacture of such catalyst, which process comprises heating the catalyst in the form of geometric shapes in an inert atmosphere prior to exposing the catalyst in the form of such shapes to an oxygen-containing atmosphere at an elevated temperature, and a process for oxidizing a feedstock comprising a hydrocarbon, such as benzene, n-butane, butenes, butadiene, or mixtures thereof, to maleic anhydride in the presence of such catalyst.

DESCRIPTION AND PREFERRED EMBODIMENTS

The catalyst of the present invention is suitably prepared in organic solvents by slurrying vanadium compounds and metals or metal oxides, such as molybdenum oxide, zinc oxide, uranium oxide, tungsten oxide, tin oxide, bismuth oxide, titanium oxide, niobium oxide, antimony oxide, and cobalt oxide, in organic solvents, such as alcohols, carboxylic acids, aldehydes, ketones, ethers, epoxides, oxygenated olefinic organic liquids, and halogenated olefinic organic liquids. The preferred solvents are organic ether solvents.

A small amount of water or a hydrogen donor compound, such as a lower alcohol, is also present in the ether. Suitable alcohols are aliphatic alcohols having from about 1 to about 8 carbon atoms per molecule. Preferred alcohols are ethanol and methanol. Suitable organic ether solvents are ethers having from about 2 to about 10 carbon atoms per molecule. Preferred ethers are tetrahydrofuran (THF), tetrahydropyran, 1,2-dimethoxyethane, bis(2-methoxyethyl)ether, 1,4-dioxane, ethylether, propylether, butylether, and pentylether. Phosphoryl halide is slowly added to the slurry. The water or hydrogen donor reacts with the phosphoryl halide to generate anhydrous phosphoric acid or phosphate esters and hydrogen halide gas. The hydrogen halide dissolves both the vanadium compound, for example, the vanadium pentoxide, and the co-metal compound and also reduces the vanadium from a valence state of about five to a valence state of about four. This reaction takes place at a temperature of about 0° C. (32° F.) to about 200° C. (392° F.).

While the reaction solution is being refluxed, if desired, a modifier or mixture of modifiers, such as o-xylene, m-xylene, p-xylene, benzene, toluene, mesitylene, pseudocumene, phthalic anhydride, trimellitic anhydride, benzoic acid, toluic acid, phthalic acid, isophthalic acid, terephthalic acid, trimesic acid, or trimellitic acid, is suitably added to the reaction solvent. After refluxing, the resulting intermediate composition, which is probably a suspension, has a green color. Preferably, the intermediate composition is heated under an atmosphere of air, nitrogen, or an air-nitrogen mixture to reduce the volume of the intermediate composition and to form a thick syrup. Optionally, the volume of the intermediate composition may be reduced by distillation or stripping until it becomes a thick syrup. This syrup is dried at a temperature of about 130° C. (266° F.) to about 200° C. (392° F.) and to 15 inches of mercury vacuum under an air purge or an air-nitrogen purge. Once dry, the color of the solid material is brown.

This solid material is a powdery material, i.e., it can be reduced easily to a powder. A treatment, such as grinding, is suitably used to reduce the solid material to a powder, typically, a material that will pass through a 30-mesh screen. The powder may be calcined suitably in air or a nitrogen-air combination at a temperature within the range of about 300° C. (572° F.) to about 370° C. (698° F.) in a rotary calciner or a fluid bed. The catalyst can be formed into geometric forms or shapes, such as cylinders, using graphite, Sterotex, or other lubricants, such as stearic acid, zinc stearate, or starch, and binders, such as polyvinyl alcohol. The catalyst in the form of geometric shapes, typically tablets, is heated in an inert atmosphere at a temperature in the range of about 343° C. (650° F.) to about 704° C. (1,300° F.). According to the present invention, the catalyst in the form of geometric shapes must be treated in the inert atmosphere prior to being exposed to an oxygen-containing gas at an elevated temperature. Such treatment in the inert atmosphere is critical to the catalyst in the form of geometric shapes in order to minimize expansion of the shaped catalyst particles resulting from subsequent exposure to oxygen-containing atmospheres at elevated temperatures.

The catalyst is activated by the addition of water and phosphorus compounds, such as alkylphosphates, phosphites, phosphines, or mixtures thereof, in the presence of the feedstock. This activation takes place at a temperature within the range of about 300° C. (572° F.) to about 500° C. (932° F.). Representative phosphorus compounds have the following structure:

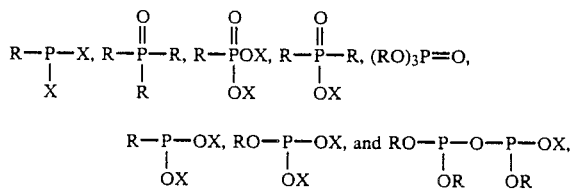

wherein R is phenyl or an alkyl radical of 1 to 6 carbon atoms and X is H or R. Suitable compounds are the primary, $RPH_2$, secondary, $R_2PH$, and tertiary, $R_3P$, phosphines, such as ethyl phosphine; the tertiary phosphine oxides, $R_3PO$, such as tripropyl phosphine oxide; the primary, $RP(O)(OX)_2$, and secondary, $R_2P(O)OX$, phosphonic acids, such as benzene phosphonic acid; the esters of the phosphonic acids, such as diethyl methanephosphonate; the phosphonous acids, $RPO_2X_2$, such as benzenephosphonous acid, and the esters thereof, such as the monoethyl ester; the phosphinous acids, $R_2POX$, such as diethyl phosphinous acid, and the esters thereof, such as the monoethyl ester; the primary, $ROP(OX)_2$, secondary, $(RO)_2POX$, and tertiary, $(RO)_3P$, phosphites, such as diethyl phosphite, trimethyl phosphite, triethyl phosphite, triisopropyl phosphite, tripropyl phosphite, and tributyl phosphite, and the pyrophosphites, such as tetraethyl pyrophosphite. The preferred phosphorus compound is an ester of orthophosphoric acid having the formula $(RO)_3P=O$, wherein R is hydrogen or a $C_1$-$C_4$ alkyl, at least one R being a $C_1$-$C_4$ alkyl. The preferred phosphorus compounds are triethylphosphate and trimethylphosphate.

The novel catalyst for the production of maleic anhydride comprising a phosphorus-vanadium mixed oxide or a phosphorus-vanadium-co-metal mixed oxide and existing in the form of geometric shapes is heated at a temperature within the range of about 343° C. (650° F.) to about 704° C. (1,300° F.) in an inert atmosphere before being used as a catalyst for the production of maleic anhydride. The usual inert gas is nitrogen, but helium and other inert gases can be utilized. It should be noted that if the catalyst in the form of geometric shapes is heated in air initially, catalysts are formed which will expand and in some instances may expand to the point of being crushed in a tubular reactor. These catalysts cannot be used in commercial operations requiring fixed bed reactors wherein the catalysts are charged into steel tubes because the pressure drop across the catalyst bed will be excessive.

The novel catalyst comprises a phosphorus-vanadium mixed oxide or a phosphorus-vanadium mixed oxide promoted by metals. The atomic ratio of the vanadium to phosphorus can suitably be in the range of 0.5:1 to 1.25:1. The total atomic ratio of vanadium to phosphorus advantageously is in the range of 0.75:1 to 1:1. It is preferred that the total atomic ratio of molybdenum, zinc, tungsten, uranium, tin, bismuth, titanium, niobium, or cobalt to vanadium should be within the range of 0.001:1 to 0.2:1.

The co-metal, such as molybdenum, zinc, tungsten, uranium, bismuth, titanium, antimony, niobium, cobalt, or tin, may be added as a compound together with vanadium or introduced separately into the solution. Suitable co-metal compounds comprise their oxides and soluble salts. Suitable molybdenum compounds comprise molybdenum oxide and most soluble molybdenum salts.

If it is desired to improve physical properties of the catalysts, they may be treated with the suspension of an inert support, for example, alumina, titania, silicon carbide, kieselguhr, pumice, or silica. The catalyst may be reinforced with such materials at any stage in its preparation.

During the preparation of the catalyst of the present invention, the average valence of vanadium is in the range of about 3.8 to 4.2. In the catalyst preparation, various phosphoryl halides may be used, but $POCl_3$ is preferred. As described hereinabove, the catalyst can be activated in the presence of water and a selected phosphorus-containing compound.

The amount of water added is about 1,000 to about 40,000 parts per million of the reaction feed gas stream. The reaction feed gas stream comprises hydrocarbon and air.

Suitable vanadium compounds include: vanadium oxides, such as vanadium pentoxide, vanadium trioxide, and the like; vanadium oxyhalides, such as vanadyl chloride, vanadyl dichloride, vanadyl trichloride, vanadyl bromide, vanadyl dibromide, vanadyl tribromide, and the like; vanadium-containing acids, such as metavanadic acid, pyrovanadic acid, and the like; vanadium salts, such as ammonium meta-vanadate, vanadium sulfate, vanadium phosphate, vanadyl formate, vanadyl oxalate, and the like; however, vanadium pentoxide is preferred.

According to the present invention, there is provided a catalyst for the production of maleic anhydride by the oxidation of a feedstock comprising a member selected from the group consisting of benzene, n-butane, butenes, butadiene, and mixtures thereof, which catalyst comprises a phosphorus-vanadium mixed oxide and exists in the form of geometric shapes, said catalyst in the form of said geometric shapes having been heated in an inert atmosphere at a temperature in the range of about 343° C. (650° F.) to about 704° C. (1,300° F.) prior to being exposed to an oxygen-containing atmosphere at an elevated temperature.

There is provided also a process for the manufacture of a catalyst comprising a phosphorus-vanadium mixed oxide, which catalyst is suitable for use in the manufacture of maleic anhydride from a feedstock comprising a member selected from the group consisting of benzene, n-butane, butenes, butadiene, and mixtures thereof, which process comprises: (1) reacting at a temperature within the range of about 0° C. (32° F.) to about 200° C. (392° F.) a vanadium compound in an organic solvent with a phosphoryl halide in the presence of water or an aliphatic alcohol having from about 1 to about 8 carbon atoms per molecule to form an intermediate composition; (2) refluxing said intermediate composition; (3) reducing the volume of said intermediate composition by heating under an atmosphere of air, inert gas, or air-inert gas mixture to form a thick syrup; (4) drying said syrup to form a solid powdery material; (5) grinding said solid powdery material to form a powder; (6) forming said powder into geometric shapes; and (7) heating said geometric shapes at a temperature within the range of about 343° C. (650° F.) to about 704° C. (1,300° F.) in an inert atmosphere prior to exposing said geometric shapes to an oxygen-containing atmosphere at an elevated temperature.

This invention also comprises a process for oxidizing a feedstock comprising a hydrocarbon, such as n-butane, to maleic anhydride by contacting it in the presence of oxygen with the novel catalyst. Accordingly, there is provided a process for oxidizing a feedstock comprising a member selected from the group consisting of benzene, n-butane, butenes, butadiene, and mixtures thereof to maleic anhydride, which process comprises contacting said feedstock in a reaction zone under suitable conditions and in the presence of an oxygen-containing gas with a catalyst comprising a phosphorus-vanadium mixed oxide and existing in the form of geometric shapes, said catalyst in the form of said geometric shapes having been heated in an inert atmosphere at a temperature within the range of about 343° C. (650° F.) to about 704° C. (1,300° F.) prior to being exposed to an oxygen-containing atmosphere at an elevated temperature.

The oxidation of the hydrocarbon to maleic anhydride may be accomplished by contacting the hydrocarbon in relatively low concentration in oxygen with the described catalyst. Air is entirely satisfactory as a source of oxygen, but synthetic mixtures of oxygen and diluent gases, such as nitrogen, also may be employed. Air enriched with oxygen may be used.

The gaseous feed stream to the oxidation reactors will normally contain air and about 0.2 to about 1.7 mole percent of n-butane, when n-butane is used as the hydrocarbon. About 0.8 to 1.5 mole percent of n-butane is satisfactory for optimum yield of maleic anhydride for the process of this invention. Although higher concentrations may be employed, explosive hazards may be encountered. Lower concentrations of butane, less than about one percent, of course, will reduce the total yield obtained at equivalent flow rates and, thus, are not normally economically employed.

The flow rate of the gaseous stream through the reactor may be varied within rather wide limits. A typical gas hourly space velocity or volumetric hourly space velocity (VHSV) is within the range of about 100 to about 4,000 cc of feed per cc of catalyst per hour ($hr^{-1}$). Preferably, the VHSV of the gaseous stream is within the range of about 500 $hr^{-1}$ to about 3,000 $hr^{-1}$ and, more preferably, about 1,000 $hr^{-1}$ to about 2,400 $hr^{-1}$. Residence times of the gas stream will normally be less than about four seconds, more preferably, less than about one second, and down to a rate where less efficient operations are obtained. The flow rates and residence times are calculated at standard conditions of 760 mm of mercury and 0° C. (32° F.).

A variety of reactors will be found to be useful, and multiple-tube heat exchanger-type reactors are quite satisfactory. The tops of such reactors may vary in diameter from about ¼ inch to about 3 inches, and the length may be varied from about 3 feet to about 10 or more feet.

The oxidation reaction is an exothermic reaction and, therefore, relatively close control of the reaction temperatures should be maintained. It is desirable to have the surface of the reactors at relatively constant temperatures, and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrate eutectic constant temperature mixture. An additional method of temperature control is to use a metal block reactor whereby the metal surrounding the tube acts as a temperature-regulating body. As will be recognized by one skilled in the art, the heat exchanger medium may be kept at the proper temperature by heat exchangers, and the like.

The reactor or reaction tubes may be iron, stainless steel, carbon steel, nickel, glass tubes, such as vycor, and the like. Both carbon steel and nickel tubes have excellent long life under the conditions of the reaction described herein. Normally, the reactors contain a preheat zone under an inert material such as ¼ inch Alundum pellets, inert ceramic balls, nickel balls, or chips, and the like, present at about one-half to one-tenth the volume of the active catalyst present.

The temperature of reaction may be varied within some limits, but normally the reaction should be conducted at a temperature within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than 20°–50° F. above the salt bath temperature. The temperature of the reactor, of course, will also depend to some extent upon the size of the reactor and the butane concentration.

Typically, the catalyst temperature is within the range of about 343° C. (650° F.) to about 540° C. (950° F.), preferably, within the range of about 371° C. (700° F.) to about 427° C. (800° F.), and, more preferably, within the range of about 393° C. (740° F.) to about 416° C. (780° F.).

The reaction may be conducted at atmospheric, superatmospheric, or subatmospheric pressure. The exit pressure will be at least slightly higher than the ambient pressure to ensure a positive flow from the reactor. The pressure of the inert gases must be sufficiently high to overcome the pressure drop through the reactor. Typically, the pressure is maintained within the range of about 14.7 psia to about 55 psia, preferably, within the range of about 20 psia to about 45 psia, and, more preferably, within the range of about 25 psia to about 40 psia.

Maleic anhydride may be recovered by a number of ways well-known to those skilled in the art. For example, the recovery may be by direct condensation or by absorption in suitable media, with specific operations and purification of the maleic anhydride.

The phosphorus-vanadium mixed oxide catalyst can be regenerated by the addition of a phosphorus compound. Typical phosphorus compounds are those that are mentioned hereinabove for use in the activation of the catalyst. Such regeneration can be continuous, i.e., the phosphorus compound, preferably an alkyl ester of orthophosphoric acid, can be added continuously with the reactor feedstream. In U.S. Pat. No. 4,649,205, Edwards discloses that, in general, the amount of alkyl ester added is about 0.1 to about 10,000 ppm (wt) of the reactor feed gas stream, that in a process using continuous catalyst regeneration, the amount of alkyl phosphate added is within the range of about 0.1 to about 30 ppm (wt) of the reactor feedstream, and that in a batch catalyst regeneration process, generally concentrations above about 30 ppm (wt) are useful, preferably concentrations within a range of about 50 ppm (wt) to about 100,000 ppm (wt) of reactor feed gas stream. Such regeneration or reactivation is conducted conveniently at a temperature within the range of about 343° C. (650° F.) to about 482° C. (900° F.). The alkyl phosphate in a water medium comprising about 0.001 to about 90 wt %, preferably about 0.01 to about 50 wt %, of the solution is contacted with the feed gas stream flowing to the reactor. Alternatively, the water and alkyl phosphate are added separately to the feed gas stream instead of as a solution or are added directly to the hydrocarbon stream prior to the mixing of the hydrocarbon and oxygen-containing reactants.

Maleic anhydride is currently produced by fixed bed catalytic oxidation of butane over mixed vanadium oxide catalyst. The catalyst is usually formed into tablets prior to loading in the multitubular reactor. The size and shape of these tablets are important since they determine the void fraction available in the reactor. It is important that this void fraction be large enough to avoid development of a large pressure drip across the reactor. One such suitable tablet is right cylinder. In addition to its dependence on the shape and dimensions of the tablet, the reactor's void fraction depends on whether those dimensions change under hydrocarbon conversion conditions. For example, if the tablet undergoes a volume increase or "expansion," the void fraction will decrease and an unacceptable increase in pressure drop will result.

It has been discovered that catalyst tablets may undergo undesirable expansion if they are heated at high temperatures, e.g., temperatures in excess of 343° C. (650° F.), in the presence of air or other oxygen-containing gases. Such conditions exist in a standard expansion test, which is described in more detail below, or in a pilot plant or commercial maleic anhydride reactor, particularly under reactor start-up conditions. The maleic anhydride catalysts may be subjected to temperatures in excess of 427° C. (800° F.) in the presence of air during these procedures and it is during this treatment that catalyst expansion occurs.

However, it has been discovered, unexpectedly, that the undesirable catalyst expansion can be reduced greatly or eliminated entirely if the catalyst tablet or powder is first pre-treated at high temperatures in the presence of an inert or substantially inert atmosphere, such as nitrogen, helium, or other inert gas. The temperature for the pretreatment of this invention is in the range of about 343° C. (650° F.) to about 704° C. (1,300° F.), more preferably, in the range of about 371° C. (700° F.) to about 482° C. (900° F.), and most preferably within the range of about 399° C. (750° F.) to about 427° C. (800° F.). After this pretreatment, the catalyst can be subjected to the conditions of the standard expansion test, or to pilot-plant or commercial reactor start-up or operating conditions, without undergoing undesirable catalyst expansion. It is necessary to conduct this catalyst pretreatment in the inert atmosphere before the catalyst in the form of geometric shapes is exposed to air or other oxygen containing gas at high temperatures or else excessive catalyst expansion will occur.

Examples of the catalyst and process of this invention are presented hereinbelow in order to facilitate a better understanding of the invention. It is to be understood that these examples are provided to illustrate some of the embodiments of this invention and are not intended to limit the scope of the invention.

Typical Catalyst Preparation

To a 3-liter, 3-neck, round bottom flask equipped with a thermowell, electrical mantle, mechanical stirrer, and reflux condenser, are added 364 grams $V_2O_5$, 17.28 grams $MoO_3$, 270 grams water, and 1,000 milliliters tetrahydrofuran (THF). Phosphoryl chloride ($POCl_3$) (767 grams) is added from an additional funnel over a period of 2 hours. During the $POCl_3$ addition, an exothermic reaction occurs which results in a continuous temperature rise, reflux of the solvent, and dissolution of the solids. The mixture turns from a yellow orange slurry to red brown solution as the $POCl_3$ addition progresses. At the end of $POCl_3$ addition, the deep green solution is heated up to reflux and maintained at reflux for 2 hours. The deep green solution is then optionally partially (500 milliliters) stripped of solvent. The thick black, green syrup is then dried overnight at about 3 inches of Hg vacuum with a mild air, nitrogen, or nitrogen-air purge passing through the oven. Drying temperature and time vary from 130° C. (266° F.) to 200° C. (392° F.) and 18 to 48 hours, respectively.

The dark brown catalyst powder is ground, calcined at 300° C. (572° F.) in air for 4 hours and formed into 3/16 in cylindrical tablets using 5 wt % graphite as a lubricant. The side crush strength of the tablets is about 5.9 pounds.

Expansion Test

In an expansion test, the length and diameter of 10 tablets are measured with a caliper. An average volume is determined using the volume relationship for a cylinder. The tablets are then introduced into an oven at 482° C. (900° F.). The tablets are kept at that temperature in a humid air stream for 2 hours. The tablets are removed from the oven and allowed to cool in a desiccator. The length and diameter of the tablets are measured and an average volume is determined. The comparison of the average volume of the tablet before and after introduction into the oven determines whether the tablets expanded, shrank, or remained the same.

EFFECT OF PRETREATMENT CONDITIONS ON TABLET VOLUME CHANGE: EXAMPLES 1-9

The effect of atmosphere and temperature on tablet volume change was determined in the following manner. The average volume of 60 tablets was determined by using the average length and diameter of all tablets and applying the volume relationship of a cylinder. These tablets (9.7 cc) were then loaded into a 0.62-inch diameter minireactor. After gas flow was established at a volume hourly space velocity (VHSV) of 1,200 hr$^{-1}$, the temperature was raised from ambient to target in about 30 to 45 minutes and held there for 2 hours. The reactor was then cooled and the tablets were removed. The volume of the tablets was then determined by using the average length and diameter of all pretreated tablets and applying the volume relationship for a cylinder. Tablet volume change of pretreated tablets was calculated relative to the volume of fresh tablets. The pretreatment atmosphere and temperature and tablet volume change are shown in Table I. The data clearly show that the inert atmosphere pretreatments result in larger tablet shrinkage than air pretreatments.

STANDARD TABLET EXPANSION TEST TO DETERMINE VOLUME CHANGES OF PRETREATED TABLETS: EXAMPLES 10-20

The invention is only useful if pretreated tablets do not expand further when subjected to a standard tablet expansion test. Experience has taught that tablet volume changes observed in such a test correlate well with tablet volume changes observed in pilot plant runs. The expansion test was carried out in the following manner. The average volume of 10 tablets from each of Examples 1-9 was determined. The tablets were then introduced into an oven, which was already set at 482° C. (900° F.), and kept therein a humid air stream for 2 hours. The tablets were then removed from the oven and allowed to cool in a desiccator. The length and diameter of the tablets were measured and the average volume was determined. This average volume was then compared with the volume of the fresh tablets prior to pretreatments described in Examples 1-9.

As shown in Table II, the air pretreated tablets underwent significant tablet expansion, while tablet shrinkage was observed for tablets pretreated in nitrogen and helium at temperatures of 427° C. (800° F.) and 482° C. (900° F.). The inert atmosphere pretreatment at 371° C. (700° F.) appears to be less adequate than such pretreatment at higher pretreatment temperatures, since the tablets pretreated in the inert atmospheres at 371° C. (700° F.) showed a positive volume change or expansion in the standard expansion test.

It appears then that a pretreatment temperature limit exists below which the invention is least preferred. In order that this limit be determined, pretreatments were conducted at 399° C. (750° F.) in nitrogen and in air, Examples 19 and 20, respectively. The pretreated tablets were then subjected to the same standard expansion test. The results are shown in Table III. The data show that the net volume change for the nitrogen-pretreated tablets is a desired shrinkage, while that of the air-pretreated tablets is an undesired and significant expansion. Because of the small tablet volume change observed for the 399° C. (750° F.)/N$_2$ pretreatments, the most preferred pretreatment temperature appears to be in the range of 399° C. (750° F.) to 427° C. (800° F.).

Butane to Maleic Anhydride Conversion of Pretreated Tablets

The catalytic performance of some of the pretreated tablets was determined in a minireactor test. A 6-cc-charge of the pretreated tablets was loaded into a 0.62 inch diameter minireactor and evaluated with a feed of 1.1 mole % n-butane in synthetic air at a VHSV of 1,200 hr$^{-1}$. About 10,000 ppm of water were continually added to the reactor feedstream by passing it through a water saturator. The data are shown in Table IV.

The data show that, relative to air pretreatment, the inert atmosphere pretreatment at 427° C. (800° F.) did not result in a detrimental effect on catalytic performance. Furthermore, all catalysts exhibited very good selectivity and yield to maleic anhydride.

TABLE I

Tablet Volume Change as a Function[1] of Temperature and Atmosphere

| Example No. | Atmosphere | Temperature, °C.(°F.) | Tablet Volume Change, %[2] |
|---|---|---|---|
| 1 | Air | 371 (700) | +0.61 |
| 2 | | 427 (800) | +2.18 |
| 3 | | 482 (900) | +6.15 |
| 4 | N$_2$ | 371 (700) | -5.04 |
| 5 | | 427 (800) | -2.23 |
| 6 | | 482 (900) | -2.56 |
| 7 | He | 371 (700) | -4.82 |
| 8 | | 427 (800) | -5.41 |
| 9 | | 482 (900) | -3.33 |

Notes:
[1] In any experiment, about 9.7 cc of tablets (60 tablets) were subjected to gas flow (VHSV = 1,200 hr$^{-1}$ at the indicated temperature for two hours.
[2] Tablet volume change is relative to the volume of fresh tablets.

TABLE II

Net Tablet Volume Change of Pretreated Tablets[1] as a Result of a Standard Tablet Expansion Test

| Example No. | Pretreatment, °C.(°F.) | Tablet Volume Change, %[2] |
|---|---|---|
| 10 | Air, 371 (700) | +8.10 |
| 11 | Air, 427 (800) | +10.10 |
| 12 | Air, 482 (900) | +9.46 |
| 13 | N$_2$, 371 (700) | +3.3 |
| 14 | N$_2$, 427 (800) | -2.36 |
| 15 | N$_2$, 482 (900) | -3.93 |
| 16 | He, 371 (700) | +8.04 |
| 17 | He, 427 (800) | -3.93 |
| 18 | He, 482 (900) | -4.24 |

Notes:
[1] Tablet volume change was obtained in a standard tablet expansion test.
[2] Tablet volume change is the net change relative to volume of fresh tablets prior to treatment.

TABLE III

Net Volume Change of Pretreated Tablets as a Result of a Standard Tablet Expansion Test

| Example No. | Pretreatment, °C.(°F.) | Tablet Volume Change[1] |
|---|---|---|
| 19 | N$_2$, 399° C.(750° F.) | -0.19 |
| 20 | Air, 399° C.(750° F.) | +8.7 |

Note:
[1] Tablet volume change is the net change relative to volume of fresh tablets prior to pretreatment.

TABLE IV

Butane Conversion to Maleic Anhydride Performance of Pretreated Catalyst

| Catalyst from Example | 2 | 5 | 8 |
|---|---|---|---|
| Pretreatment Atmosphere | Air | N$_2$ | He |

TABLE IV-continued

Butane Conversion to Maleic Anhydride
Performance of Pretreated Catalyst

| Catalyst from Example | 2 | 5 | 8 |
|---|---|---|---|
| Pretreatment Temperature, °F. | 800 | 800 | 800 |
| °C. | 427 | 427 | 427 |
| Hours on Stream | 192 | 192 | 192 |
| Temperature, °F. | 791 | 791 | 789 |
| °C. | 422 | 422 | 421 |
| Conversion, Mole %[1] | 84 | 83 | 82 |
| Selectivity, Mole %[2] | 64 | 64 | 64 |

Note:

[1]Conversion, % = $\frac{\text{moles n-butane reacted}}{\text{moles n-butane in feed}} \times 100$

[2]Selectivity, % = $\frac{\text{moles maleic anhydride produced}}{\text{moles n-butane consumed}} \times 100$

What is claimed is:

1. A catalyst for the production of maleic anhydride by the oxidation of a feedstock comprising a member selected from the group consisting of benzene, n-butane, butenes, butadiene and mixtures thereof, which catalyst comprises a phosphorus-vanadium mixed oxide and exists in the form of geometric shapes, said catalyst in the form of said geometric shapes having been heated in an inert atmosphere at a temperature within the range of about 343° C. (650° F.) to about 704° C. (1,300° F.) prior to being exposed to an oxygen-containing atmosphere at an elevated temperature wherein said phosphorus-vanadium mixed oxide catalyst has an atomic ratio of vanadium-to-phosphorus in the range of about 0.5:1 to about 1.25:1.

2. The catalyst of claim 1, wherein said catalyst comprises further a co-metal as a promoter, said co-metal being a member selected from the group consisting of molybdenum, zinc, tungsten, uranium, bismuth, titanium, antimony, niobium, cobalt, and tin, and the ratio of said co-metal to vanadium being within the range of about 0.001:1 to about 0.2:1.

3. A phosphorus-vanadium mixed oxide catalyst for the production of maleic anhydride by the oxidation of a feedstock comprising a member selected from the group consisting of benzene, n-butane, butenes, butadiene, and mixtures thereof, wherein said catalyst is prepared by a process which comprises reacting at a temperature within the range of about 0° C. (32° F.) to about 200° C. (392° F.) a vanadium compound in an organic solvent with a phosphoryl halide in the presence of water or an aliphatic alcohol having from about 1 to about 8 carbon atoms per molecule to form an intermediate composition; refluxing said intermediate composition; reducing the volume of said intermediate composition by heating under an atmosphere of air, inert gas, or air-inert gas mixture to form a thick syrup; drying said syrup to form a solid powdery material; treating said solid powdery material to form a powder; forming said powder into geometric shapes; and heating said geometric shapes at a temperature within the range of about 343° C. (650° F.) to about 704° C. (1,300° F.) in an inert atmosphere prior to exposing said geometric shapes to an oxygen-containing atmosphere at an elevated temperature.

4. The catalyst of claim 1, wherein said catalyst is activated by the process which comprises treating it in the presence of a feedstock comprising benzene, n-butane, butenes, butadiene, or mixtures thereof and at a temperature within the range of about 300° C. (572° F.) to about 500° C. (932° F.) with water and a phosphorus compound selected from the group consisting of compounds having the following structures:

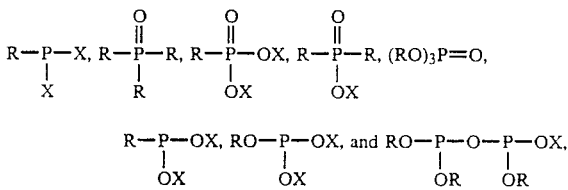

wherein R is phenyl or an alkyl radical of 1 to 6 carbon atoms and X is H or R.

5. The catalyst of claim 1, wherein said temperature at which said catalyst in the form of geometric shapes is heated in an inert atmosphere is a temperature within the range of about 371° C. (700° F.) to about 482° C. (900° F.).

6. The catalyst of claim 1, wherein said geometric shapes comprise tablets.

7. The catalyst of claim 2, wherein said co-metal is molybdenum.

8. The catalyst of claim 2, wherein said co-metal is zinc.

9. The catalyst of claim 3, wherein said vanadium compound is a member selected from the group consisting of vanadium oxides, vanadium oxyhalides, vanadium-containing acids, and vanadium salts, said organic solvent is an organic ether solvent having from about 2 to about 10 carbon atoms per molecule, and said geometric shapes comprise tablets.

10. The catalyst of claim 3, wherein said catalyst is activated by the process which comprises treating it in the presence of a feedstock comprising benzene, n-butane, butenes, butadiene, or mixtures thereof and at a temperature within the range of about 300° C. (572° F.) to about 500° C. (932° F.) with water and a phosphorus compound selected from the group consisting of compounds having the following structures:

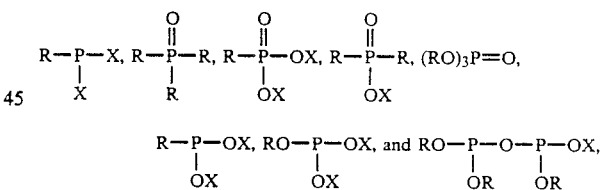

wherein R is phenyl or an alkyl radical of 1 to 6 carbon atoms and X is H or R.

11. The catalyst of claim 4, wherein said phosphorus compound is an alkylester of orthophosphoric acid and has the following structure:

$(RO)_3P=O$, wherein R is hydrogen or a $C_1$ to $C_4$ alkyl radical, at least one R being a $C_1$ to $C_4$ alkyl radical.

12. The catalyst of claim 7, wherein said temperature at which said catalyst in the form of geometric shapes is heated in an inert atmosphere is a temperature within the range of about 371° C. (700° F.) to about 482° C. (900° F.).

13. The catalyst of claim 3, wherein molybdenum is added as a co-metal promoter and wherein the ratio of molybdenum to vanadium is within the range of about 0.001:1 to about 0.2:1.

14. The catalyst of claim 7, wherein said catalyst is activated by the process which comprises treating it in the presence of a feedstock comprising benzene, n-butane, butenes, butadiene, or mixtures thereof and at a temperature within the range of about 300° C. (572° F.) to about 500° C. (932° F.) with water and a phosphorus compound selected from the group consisting of compounds having the following structures:

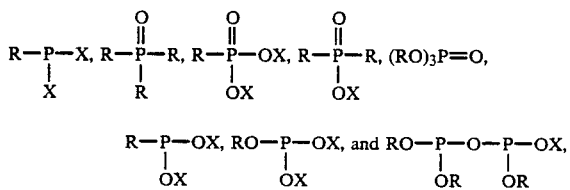

wherein R is phenyl or an alkyl radical of 1 to 6 carbon atoms and X is H or R.

15. The catalyst of claim 9, wherein said vanadium compound is vanadium pentoxide, said phosphoryl halide is phosphoryl chloride, and said organic ether solvent is tetrahydrofuran.

16. The catalyst of claim 10, wherein said phosphorus compound is an alkylester of orthophosphoric acid and has the following structure:

$(RO)_3P=O,$ wherein R is hydrogen or a $C_1$ to $C_4$ alkyl radical, at least one R being a $C_1$ to $C_4$ alkyl radical.

17. The catalyst of claim 13, wherein said vanadium compound is a member selected from the group consisting of vanadium oxides, vanadium oxyhalides, vanadium-containing acids, and vanadium salts, said organic solvent is an organic ether solvent having from about 2 to about 10 carbon atoms per molecule, and said geometric shapes comprise tablets.

18. The catalyst of claim 13, wherein said catalyst is activated by the process which comprises treating it in the presence of a feedstock comprising benzene, n-butane, butenes, butadiene, or mixtures thereof and at a temperature within the range of about 300° C. (572° F.) to about 500° C. (932° F.) with water and a phosphorus compound selected from the group consisting of compounds having the following structures:

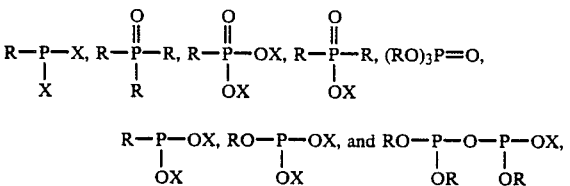

wherein R is phenyl or an alkyl radical of 1 to 6 carbon atoms and X is H or R.

19. The catalyst of claim 14, wherein said phosphorus compound is an alkylester of orthophosphoric acid and has the following structure:

$(RO)_3P=O,$ wherein R is hydrogen or a $C_1$ to $C_4$ alkyl radical, at least one R being a $C_1$ to $C_4$ alkyl radical.

20. The catalyst of claim 17, wherein said vanadium compound is vanadium pentoxide, said phosphoryl halide is phosphoryl chloride, and said organic ether solvent is tetrahydrofuran.

21. The catalyst of claim 18, wherein said phosphorus compound is an alkylester of orthophosphoric acid and has the following structure:

$(RO)_3P=O,$ wherein R is hydrogen or a $C_1$ to $C_4$ alkyl radical, at least one R being a $C_1$ to $C_4$ alkyl radical.

22. A process for the manufacture of a catalyst comprising a phosphorus-vanadium mixed oxide, which catalyst is suitable for use in the manufacture of maleic anhydride from a feedstock comprising a member selected from the group consisting of benzene, n-butane, butenes, butadiene, and mixtures thereof, which process comprises: (1) reacting at a temperature within the range of about 0° C. (32° F.) to about 200° C. (392° F.) a vanadium compound in an organic solvent with a phosphoryl halide in the presence of water or an aliphatic alcohol having from about 1 to about 8 carbon atoms per molecule to form an intermediate composition; (2) refluxing said intermediate composition; (3) reducing the volume of said intermediate composition by heating under an atmosphere of air, inert gas, or air-inert gas mixture to form a thick syrup; (4) drying said syrup to form a solid powdery material; (5) grinding said solid powdery material to form a powder; (6) forming said powder into geometric shapes; and (7) heating said geometric shapes at a temperature within the range of about 343° C. (650° F.) to about 704° C. (1,300° F.) in an inert atmosphere prior to exposing said geometric shapes to an oxygen-containing atmosphere at an elevated temperature.

23. The process of claim 22, wherein distillation or stripping is employed to reduce the volume of said intermediate composition.

24. The process of claim 22, wherein said process comprises reacting said vanadium compound with said phosphoryl halide in the presence of a co-metal compound to form a catalyst comprising a phosphorus-vanadium-co-metal-mixed oxide catalyst.

25. The process of claim 22, wherein the geometric shapes of said catalyst comprise tablets.

26. The process of claim 22, wherein said vanadium compound is a member selected from the group consisting of vanadium oxides, vanadium oxyhalides, vanadium-containing acids, and vanadium salts, and said organic solvent is an organic ether solvent having from about 2 to about 10 carbon atoms per molecule.

27. The process of claim 22, wherein said temperature at which said geometric shapes are heated in an inert atmosphere is a temperature within the range of about 371° C. (700° F.) to about 482° C. (900° F.).

28. The process of claim 24, wherein said co-metal compound is a compound of molybdenum and said catalyst comprises a phosphorus-vanadium-molybdenum-mixed oxide catalyst.

29. The process of claim 24, wherein said co-metal compound is a compound of zinc and said catalyst comprises a phosphorus-vanadium-zinc-mixed oxide catalyst.

30. The process of claim 24, wherein the geometric shapes of said catalyst comprise tablets.

31. The process of claim 24, wherein said vanadium compound is a member selected from the group consisting of vanadium oxides, vanadium oxyhalides, vanadium-containing acids, vanadium salts, and said organic solvent is an organic ether solvent having from about 2 to about 10 carbon atoms per molecule.

32. The process of claim 26, wherein said vanadium compound is vanadium pentoxide, said phosphoryl halide is phosphoryl chloride, said organic ether solvent is tetrahydrofuran, and said geometric shapes comprise tablets.

33. The process of claim 28, wherein said catalyst is prepared by calcining said powder in an oxygen-containing gas prior to forming said powder into said geometric shapes.

34. The process of claim 31, wherein said vanadium compound is vanadium pentoxide, said phosphoryl halide is phosphoryl chloride, and said organic ether solvent is tetrahydrofuran.

35. The process of claim 32, wherein said catalyst is prepared by calcining said powder in an oxygen-containing gas prior to forming said powder into said geometric shapes.

36. The process of claim 33, wherein the geometric shapes of said catalyst comprise tablets.

37. The process of claim 33, wherein said vanadium compound is vanadium pentoxide, said phosphoryl halide is phosphoryl chloride, and said organic ether solvent is tetrahydrofuran.

38. The process of claim 36, wherein said vanadium compound is a member selected from the group consisting of vanadium oxides, vanadium oxyhalides, vanadium-containing acids, and vanadium salts, and said organic solvent is an organic ether solvent having from about 2 to about 10 carbon atoms per molecule.

39. The process of claim 36, wherein said temperature at which said tablets are heated in an inert atmosphere is a temperature within the range of about 371° C. (700° F.) to about 482° C. (900° F.).

40. The process of claim 38, wherein said vanadium compound is vanadium pentoxide, said phosphoryl halide is phosphoryl chloride, and said organic ether solvent is tetrahydrofuran.

41. The process of claim 40, wherein said temperature at which said tablets are heated in an inert atmosphere is a temperature within the range of about 371° C. (700° F.) to about 482° C. (900° F.).

* * * * *

UNITED STATES PATENT OFFICE
CERTIFICATE OF CORRECTION

Patent No. 4,996,179                     Dated February 26, 1991

Inventor(s) Muin S. Haddad, Bernard L. Meyers and William S. Eryman

It is certified that error appears in the above-identified patent and that said Letters Patent is hereby corrected as shown below:

| Col. | Line | |
|---|---|---|
| 10 | 42 | "+10.10" should read --+10.19-- |
| 14 | 13-14 | Type print error should read --suitable-- |
| | | Type print error should read --from-- |
| 14 | 63 | Type print error should read --process-- |
| 14 | 67-68 | Type print error should read --oxides-- |
| | | Type print error should read --acids, and-- |

Signed and Sealed this

Eighteenth Day of August, 1992

Attest:

DOUGLAS B. COMER

Attesting Officer       Acting Commissioner of Patents and Trademarks